(12) United States Patent
Zheng et al.

(10) Patent No.: US 8,951,796 B2
(45) Date of Patent: Feb. 10, 2015

(54) METHODS AND COMPOSITIONS FOR EXPANDING AND STABILIZING NATURAL REGULATORY T CELLS

(75) Inventors: Song Guo Zheng, Arcadia, CA (US); David A. Horwitz, Santa Monica, CA (US); Juhua Wong, Arcadia, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/642,811

(22) PCT Filed: Apr. 21, 2011

(86) PCT No.: PCT/US2011/033484
§ 371 (c)(1),
(2), (4) Date: Dec. 13, 2012

(87) PCT Pub. No.: WO2011/133808
PCT Pub. Date: Oct. 27, 2011

(65) Prior Publication Data
US 2013/0084269 A1    Apr. 4, 2013

Related U.S. Application Data

(60) Provisional application No. 61/326,907, filed on Apr. 22, 2010.

(51) Int. Cl.
*C12N 5/0783*   (2010.01)
*A61K 35/12*    (2006.01)

(52) U.S. Cl.
CPC .............. *A61K 35/17* (2013.01); *C12N 5/0636* (2013.01); *C12N 5/0637* (2013.01); *A61K 2035/122* (2013.01); *C12N 2501/065* (2013.01); *C12N 2501/15* (2013.01); *C12N 2501/23* (2013.01); *C12N 2501/24* (2013.01); *C12N 2501/385* (2013.01); *C12N 2501/51* (2013.01); *C12N 2501/515* (2013.01)
USPC .......................... 435/377; 435/372.3; 435/384

(58) Field of Classification Search
CPC .................. A61K 2035/122; C12N 2501/385; C12N 5/0637
See application file for complete search history.

(56) References Cited

U.S. PATENT DOCUMENTS

| | | | |
|---|---|---|---|
| 8,415,154 B2 * | 4/2013 | Noelle | 435/377 |
| 2009/0136470 A1 | 5/2009 | Cheroutre | |
| 2009/0257988 A1 | 10/2009 | Horwitz | |

OTHER PUBLICATIONS

Van et al., Diabetes. Jan. 2009;58(1):146-155.*
Lal and Bromberg, Blood. Oct. 29, 2009;114(18):3727-3735.*
Mucida, Daniel et al., "Reciprocal T(H)17 and regulatory T cell differentiation mediated by retinoic acid", Science, vol. 317, Noo. 5835, Jul. 1, 2007, pp. 256-260.
Wang, Jun et al., "De novo generation and enhanced suppression of human CD4+CD25+regulatory T cells by reinoic acid", J. of Immunoology, 2009, vol. 183, No. 6, pp. 5119-4126.
Nolting, Jens, et al., "Retinoic acid can enhance conversion of naive into regulatory T cells independently of secreted cytokines", The Journal of Experimental Medicine, 2009, vol. 206, No. 10, pp. 2131-2139.
Schambach, Felix et al., "Activation of retinoic acid receptor-alpha favours regulatory T cell induction at the expense of IL-17 secreting T helper cell differentiation", European Journal of Immunology, (2007), vol. 37, No. 9, pp. 2396-2399.
Lu, L et al., "Retinoic Acid, IL-2 and TFG-sz can Rapidly Induce Naive 13642811Human CD4+ Cells to Become CD25 +Foxp3 + Regulatory Cells with Protective Activity in vivo", Clinical Immunology, (2010), vol. 135, No. 1, pp. S31, XP027048895.
Moore, C et al., "Transforming Growth Factor-beta and All-Trans Retinoic Acid Generate Ex Vivo Transgenic Regulatory T cells With Intestinal Homing Receptors", Transplantation Proceedings, (2009), vol. 41, No. 6, pp. 2670-2672.
Xiao, S, et al., "F. 37. Retinoic Acid Increases Foxp3+ Regulatory T Cells and Inhibits Development of Th17 Cells by Enhancino TGF-b-driven Smad3 Signaling and Inhibiting, IL-6 and IL-23 Receptor Expression", Clinical Immunology, (2008), vol. 127, pp. S55, XP022615951.
Lal Girdhari et al., "Epigenetic Regulation of Foxp3 Expression in Regulatory T Cells by DNA Methylation", Journal of Immunology, (2009). vol. 182, No. 1, pp. 259-273, XP002538141.
Lu Ling et al., "Characterization of Protective Human CD4CD25 FOXP3 Regulatory T Cells Generated with IL-2, TGF-[beta] and Retinoic Acid", PLOS ONE 2010 LNKD-PUBMED:21179414, (2010), vol. 5, No. 12, pp. E15150, ZP002652171.

* cited by examiner

*Primary Examiner* — Daniel C Gamett
(74) *Attorney, Agent, or Firm* — Morgan, Lewis & Bockius LLP

(57) ABSTRACT

The present invention is directed to methods and compositions for expanding and stabilizing the phenotype of natural regulatory T cells. In particular, the present invention provides methods and compositions for treating natural regulatory T cells that renders the cells resistant to factors present in the inflammatory milieu and stabilizes the suppressive properties of the cells.

30 Claims, 12 Drawing Sheets

METHODS AND COMPOSITIONS FOR EXPANDING AND STABILIZING NATURAL REGULATORY T CELLS

CROSS-REFERENCE TO RELATED APPLICATIONS

This application is a U.S. National Phase of International Patent Application No. PCT/US2011/033484 filed Apr. 21, 2011 which claims priority to provisional application No. 61326907 filed Apr. 22, 2010, the disclosures of which are incorporated herein by reference in their entirety for all purposes.

STATEMENT REGARDING FEDERALLY SPONSORED RESEARCH

Not applicable.

BACKGROUND OF THE INVENTION

Regulatory T cells (also known as "suppressor T cells" or "Tregs") are specialized populations of T cells that act to suppress activation of the immune system and thereby maintain immune system homeostasis and tolerance to self-antigens. Regulatory T cells can occur naturally (also referred to herein as "nTregs") or they can be induced in peripheral lymphoid tissues (also referred to herein as "iTregs").

Naturally occurring, thymus derived regulatory T cells play crucial roles in controlling autoimmune disease by maintaining immunological homeostasis and self-tolerance. Adoptive transfer of nTregs has been shown to prevent many autoimmune diseases, including experimental autoimmune encephalomyelitis, colitis, diabetes and gastritis. However, the effect of transferred nTregs once a disease is established is less predictable. For example, in lupus, the effect of transferred nTregs is modest if the transfer occurs after the disease is established. Similarly, in collagen-induced arthritis, it has been shown that nTreg transfer can prevent but cannot modify the established disease. A possible reason for the lack of effect with nTregs once the disease is established may be due to an instability of FOXP3 in an inflammatory milieu, conversion of nTregs to pro-inflammatory effector cells, or an acquired resistance of T effector cells to nTregs.

For therapeutic applications, it would be advantageous to have methods and compositions for expanding nTregs with stabilized phenotypes that remain resistant to effector cell conversion after expansion.

SUMMARY OF THE INVENTION

Accordingly, the present invention provides methods and compositions for expanding natural regulatory T cells (nTregs) with stabilized phenotypes.

In one aspect, the present invention provides a method of stabilizing nTregs to become resistant to pro-inflammatory conversion. In an exemplary aspect, such a method includes treating a cell culture comprising nTregs with a regulatory composition that includes a vitamin A derivative.

In a further aspect, the present invention provides a method of stabilizing the phenotype of nTregs by treating nTregs with a regulatory composition that includes all-trans retinoic acid (atRA).

In a still further aspect, the present invention provides a method for decreasing expression of transcription factors associated with inflammatory responses in nTregs. In an exemplary aspect, such a method includes treating nTregs with a composition comprising atRA.

In a yet further aspect, the present invention provides a method for treating an aberrant immune response or an autoimmune disease in a patient by administering treated nTregs to that patient. In an exemplary aspect, the treated nTregs are generated by treating a cell culture of nTregs with a regulatory composition that includes atRA.

BRIEF DESCRIPTION OF THE DRAWINGS

FIG. 2 shows data on the effect of atRA on expression of FOXP3 in nTregs.

FIG. 3 shows data showing that nTregs treated with atRA suppress the progression of established collagen-induced arthritis.

FIG. 4 shows data on the effect of atRA treatment on nTreg phenotype and function.

FIG. 5A shows percentage of FOXP3 cells and FIG. 5B shows total numbers of FOXP3 cells treated with DMSO and atRA.

FIG. 6 shows data on the protective effects of atRA treatment in human nTregs.

FIG. 7 shows data from nTregs isolated from autoimmune arthritis (collagen-induced arthritis, "CIA") mice and treated with atRA.

DETAILED DESCRIPTION OF THE INVENTION

Figure 1A:
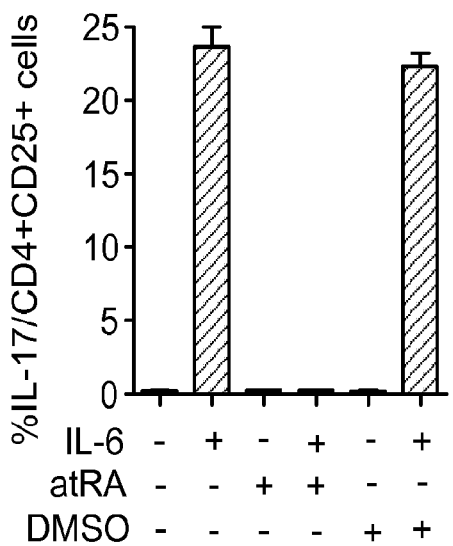
FIGS. 1A and B show percentage of IL-17 cells resulting from CD4+CD25+ cells stimulated with anti-CD3 and anti-CD28 and IL-6 with or without atRA.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview

The present invention is directed to expanding natural regulatory T cells (also referred to herein as "nTregs") and stabilizing the phenotype of nTregs.

In one aspect, nTregs are expanded and stabilized through treatment with compositions comprising one or more agents described herein and known in the art. nTregs that have been treated in accordance with the present invention are also referred to herein as "treated nTregs".

In some aspects, "stabilizing the phenotype" of nTregs includes rendering nTregs resistant to Th17 conversion, sustaining suppressive activities of nTregs even in the presence of components of inflammatory infiltrates, downregulation of IL-6R and IL-6R signaling in nTregs, downregulation of transcription factors associated with Th17 cell differentiation, or any combination thereof. Thus, as used herein, the term "treated nTregs" refers to nTregs that have been expanded and stabilized such that they are resistant to Th17 conversion and/or maintain suppressive activities in the presence of components of inflammatory infiltrates.

In a further aspect, nTregs are treated with compositions comprising a vitamin A or a derivative of vitamin A. Although nTregs do not generally metabolize vitamin A, dendritic cells can metabolize vitamin A to form all-trans retinoic acid. Cultures containing both nTregs and dendritic cells can in some embodiments be treated with vitamin A to result in the treated nTregs described in further detail herein.

In a specific embodiment, nTregs are treated using a regulatory composition comprising an active metabolite of vitamin A such as all-trans retinoic acid ("atRA"). As used herein, the term "regulatory composition" is a composition that comprises vitamin A or a vitamin A derivative (also referred to herein as a vitamin A metabolite) alone or in combination with other agents described herein that is used to expand and stabilize the phenotype of nTregs. These other agents may in some non-limiting exemplary embodiments include cytokines, T cell activators, agents that affect transcription factors, agents that affect T cell differentiation, epigenetic agents that affect acetylation and methylation of transcription factors, or any combination thereof. In a preferred embodiment, a regulatory composition of the invention is applied to a culture of nTregs to generate an expanded population of treated nTregs to produce a populations with a stabilized phenotype. As has been described in the art, a "regulatory composition" may also in some embodiments be used to induce regulatory T cells from non-regulatory T cells (see for example U.S. Ser. No. 12/421,941, filed Apr. 10, 2009, US Patent Pub. No. 20090257988, which is hereby incorporated by reference for all purposes and in particular for all teachings related to generating regulatory T cells).

Although the description provided herein primarily discusses regulatory compositions comprising atRA alone or in combination with one or more other agents, it will be appreciated that regulatory compositions of the invention may include other derivatives of vitamin A or vitamin A itself, and that the following discussion also applies to such regulatory compositions.

In still further aspects, regulatory compositions of the invention comprising atRA further include agents that affect the acetylation and methylation status of FOXP3, particularly the FOXP3 gene promoter, agents that affect the differentiation of T cells into suppressor cells, T cell activators, cytokines, or any combinations thereof.

In certain aspects, the present invention provides methods and compositions for the prevention and treatment of immune disorders or autoimmune diseases. In exemplary embodiments, the present invention provides methods in which treated nTregs are administered to patients to prevent and/or treat an immune disorder. "Immune disorder" as used herein encompasses autoimmune diseases as well as aberrant or undesired immune responses (such as graft rejection and graft versus host disease). Immune disorder also encompasses chronic immune disease triggered by a virus or other infectious agent or toxin.

As used herein, the term "patient" refers to any mammalian subject, including humans. In further embodiments, nTregs are administered along with an agent such as atRA to patients to prevent and/or treat an immune disorder.

In further aspects, the present invention provides kits for the treatment of nTregs and kits for use in the prevention and treatment of immune disorders. In some embodiments, kits of the invention include regulatory compositions of the invention, where those regulatory compositions comprise vitamin A or a derivative of vitamin A alone or in combination with other agents described herein. In further embodiments, these regulatory compositions include atRA. In still further embodiments, treated nTregs are included in kits of the invention.

II. Expansion of nTregs and Stabilization of Phenotype

In one aspect, the present invention provides methods and compositions for treating nTregs to expand the population of nTregs and stabilize the phenotype of the nTregs. nTregs are thymus-derived regulatory T cells and are generally isolated from the thymus or from peripheral blood samples. nTregs can be obtained from any mammalian subject, including humans. nTregs can be distinguished from induced Tregs ("iTregs"), because iTregs are heavily methylated, which can in some situations lead to instability. For certain applications, particularly applications in which the stability of phenotypic properties is of particular importance, the use of nTregs is preferable to that of iTregs.

In one embodiment, nTregs isolated from a patient are concentrated prior to treatment according to the methods described herein or known in the art. In a further embodiment, isolated nTregs are concentrated using cell sorting methods known in the art. In a further embodiment, after one, two, three, four, five, or more concentration steps, the cells can be washed to remove serum proteins and soluble blood components, such as autoantibodies, inhibitors, etc., using techniques well known in the art. Generally, such techniques involve addition of physiological media or buffer, followed by centrifugation. Such steps may be repeated as necessary.

In general, only a small amount of nTregs can be obtained from a patient, and it is often necessary to expand the nTregs obtained from a patient in order to have enough cells for downstream uses, such as treatment with agents as described herein and use of treated nTregs to alleviate and/or prevent immune disorders. Methods for expanding nTregs are known in the art. However, conventional methods for expanding nTregs generally do not stabilize the regulatory T cell phenotype, particularly suppressive ability.

In the present invention, "treated nTregs" are natural Tregs that have been expanded and stabilized through treatment of nTregs with a regulatory composition comprising atRA alone or in combination with one or more of the agents described herein. In general, nTregs are expanded and stabilized by applying one or more agents to a culture of nTregs.

In specific embodiments, nTregs are treated with a regulatory composition of the invention comprising a vitamin A derivative to expand the number of nTregs and stabilized their phenotype. In further embodiments, the vitamin A derivative is atRA. By "phenotype" or "phenotypic property" as used herein is meant an observable characteristic. Treatment of nTregs in accordance with the methods and compositions described herein stabilize the phenotypes of nTregs, meaning that the nTreg population becomes resistant to reduction or suppression. For nTregs, such phenotypic properties can include without limitation: expression of certain proteins (such as cytokines and transcription factors), proliferation, and suppressor activity. For example, nTregs are known to express the transcription factor FOXP3 and can express cytokines such as transforming growth factor beta (TGF-β). nTregs tend to express only low levels of other cytokines, such as interleukin 4 (IL-4) and interleukin 10 (IL-10). Cells displaying suppressor activity have also been shown to express the cytokine TGF-β on their membranes. Tregs with "suppressor activity" are cells with the ability to suppress proliferation and immune responses of other T cells.

A primary phenotypic property of nTregs is suppressor activity. Suppressor activity can be measured in a number of ways, including standard assays for T cell cytotoxic activity, such as inhibition of T cell proliferation, as well as assays described for example in U.S. Pat. No. 6,759,035, which is hereby incorporated by reference in its entirety for all purposes and in particular for all teachings related to assays of suppressor cell activity.

One phenotypic property of nTregs stabilized by treatment in accordance with the methods and compositions described herein is expression of the transcription factor FOXP3. FOXP3 is a master controller of nTregs and has been shown to be required for their development and function. Both mice and humans with a genetic deficiency of the FOXP3 gene develop autoimmune symptoms. Studies have shown that stimulation of murine non-regulatory T cells in the presence of the cytokines IL-2 and TGF-β results in expression of FOXP3 and the development of suppressor activity. Although FOXP3 expression is not an absolute indicator of suppressor activity, it is one phenotypic property that may be stabilized using the methods as described herein. In an exemplary embodiment, treatment with a regulatory composition comprising atRA alone or in combination with one or more of TGF-β, IL-2, anti-CD3, anti-CD28, or any combination thereof, stabilizes FOXP3 expression in nTregs by blocking the effect of an inflammatory milieu containing pro-inflammatory cytokines such as IL-1 and IL-6. In a specific embodiment, treated nTregs of the invention are resistant to a decrease in FOXP3 expression in the presence of IL-1 and IL-6. In contrast, nTregs expanded in the absence of atRA will show a marked decrease in FOXP3 expression in the presence of exogenous IL-1 and IL-6 (see FIG. 1D) as well as a decreased suppressive activity in an in vivo suppressor cell assay (see FIG. 1E).

Another phenotypic property of nTregs is expression of membrane-bound TGF-β. Methods for detection of membrane-bound TGF-β are described for example in U.S. patent application Ser. No. 12/194,101, filed on Aug. 19, 2008, publication number US2009/0075296, which is hereby incorporated by reference in its entirety for all purposes and in particular for all teachings related to assays for membrane-bound TGF-β. Methods and compositions of the present invention will in exemplary embodiments stabilize the expression of membrane-bound TGF-β in nTregs—that is, treated nTregs of the present invention include those with the phenotypic property of stabilized expression of membrane-bound TGF-β alone or in combination with any other phenotypic property (such as resistance to conversion) described herein.

A further phenotypic property of nTregs is poor proliferative responsiveness in vitro, which is often accompanied by lowered production of certain cytokines that enhance proliferation, such as IL-2. Other cytokines, such as IL-4, IFNγ and TFN-α are also associated with proliferation, although they are generally produced in low levels even in proliferating cells. Proliferation response can be measured using methods known in the art, such as thymidine uptake assays and assays of carboxyfluorescein succinimidyl ester (CFSE) dilution. Methods and compositions of the present invention will in exemplary embodiments stabilize this phenotypic property of nTregs—that is, treated nTregs of the present invention include those with the phenotypic property of poor proliferative response alone or in combination with any other phenotypic property (such as resistance to conversion) described herein.

A still further phenotypic property that may be stabilized using methods and compositions described herein is resistance to conversion of nTregs to Th17 cells. In an exemplary aspect, treatment of nTregs with agents described herein, including atRA with or without TGF-β, IL-2 and T cell activators, prevents intracellular and soluble IL-17 production in the presence of IL-6. IL-6 is a known component of the inflammatory milieu. Tregs that have not been treated in accordance with the methods described herein, particularly nTregs that have not been expanded in the presence of atRA, will convert to Th17 cells in the presence of IL-6 (see FIG. 1).

As discussed herein, one aspect of the present invention provides methods and compositions for treating nTregs to expand the population of nTregs and stabilize the phenotype of the nTregs. In a further aspect, nTregs are treated with a regulatory composition comprising atRA alone or in combination with one or more other agents described herein to expand the population and stabilize the phenotype. Compositions of the invention for treating nTregs can include a number of different components, as will be discussed in further detail herein.

Regulatory compositions of the invention for treating nTregs include vitamin A or a derivative of vitamin A. In certain embodiments, the derivative of vitamin A used is retinoic acid. In further embodiments, the retinoic acid is all trans retinoic acid ("atRA"). In some embodiments, other derivatives of vitamin A are used in regulatory compositions of the invention, such as vitamin A palmitate, retinal, synthetic retinoids such as AM80 (Tamibarotine), isotretinoin, and etretinate. As will be appreciated, vitamin A derivatives such as atRA can be used alone or in combination with one or more other vitamin A derivatives, with vitamin A, with any other agents described herein as well as agents known in the art to expand nTregs and stabilize their phenotype. In exemplary embodiments, regulatory compositions of the invention include from about 0.1 to about 2.0 μM of atRA or other vitamin A derivatives alone or in combination with one or more other agents described herein or known in the art. In further exemplary embodiments, regulatory compositions of the invention comprise 0.5 μM of atRA or other vitamin A derivatives alone or in combination with one or more other agents described herein or known in the art. In still further exemplary embodiments, regulatory compositions of the invention comprise 0.1, 0.3, 0.5, 0.7, 0.9, 1.1, 1.3, 1.5, 1.7, or 1.9 μM of atRA or other vitamin A derivatives alone or in combination with one or more other agents described herein or known in the art. In yet further embodiments, regulatory compositions of the invention include from about 0.01 to about 20.0 μM of atRA or other vitamin A derivatives alone or in combination with one or more other agents described herein or known in the art.

In further aspects and in accordance with any of the teachings herein, alone or in addition to vitamin A derivatives, regulatory compositions of the invention for treating nTregs may further include an agent that affects the methylation or acetylation of a transcription factor. In certain embodiments, regulatory compositions of the invention for treating nTregs further include agents that affect the acetylation and methylation status of FOXP3, particularly the FOXP3 gene promoter. In certain embodiments, regulatory compositions of the invention for treating nTregs further include agents that affect the methylation status of the gene for TGF-β. The effect on gene methylation may be through direct action of the agent on the gene or indirectly through action of the agent on one or more intermediaries. In a further embodiment, the agent prevents the methylation of the FOXP3 gene and/or the gene for TGF-β. In one aspect, the agent used to prevent methylation of the FOXP3 gene is a methyltransferase inhibitor. Such methylase transferase inhibitors can for example include without limitation azacytidine ("azaC"—also known as 2'-Deoxy-5-azacytidine; 5-Aza-2'-deoxycytidine) and 1-b-D-ribofuranosyl-2(1H)-pyrimidinone. In some embodiments, the present invention includes agents that enhance acetylation of the FOXP3 gene promoter (such as retinoic acid) and/or agents that suppress FOXP3 deacetylation (such as trichostatin A). In still further aspects, regulatory compositions of the invention may further include an agent that that enhance histone acetylation, such as trichostatin A (see Tao et al., (2007) *Nat Med* 13:1299-1307). As will be appreciated, agents that affect the acetylation and methylation status of transcription factors such as FOXP3 and TGF-β can be used alone or in combination with any other agents described herein as well as agents known in the art to expand nTregs and stabilize their phenotype.

In still further aspects, compositions of the invention for treating nTregs include one or more cytokines. In specific embodiments, such cytokines may include TGF-β, IL-2, IL-15, TNFα, individually or in any combination. As will be appreciated, such cytokines can be used alone or in combination with any other agents described herein to expand nTregs and stabilize their phenotype.

By "transforming growth factor-β" or "TGF-β" herein is meant any one of the family of the TGF-βs, including the three isoforms TGF-β1, TGF-β2, and TGF-β3; see Massague, J. (1980), *J. Ann. Rev. Cell Biol* 6:597. Lymphocytes and monocytes produce the β1 isoform of this cytokine (Kehrl, J. H. et al. (1991), *Int J Cell Cloning* 9: 438-450). The TGF-β can be any form of TGF-β that is active on the mammalian cells being treated. In humans, recombinant TGF-β is currently preferred. In general, the concentration of TGF-β used in compositions of the invention can range from about 2 pg/ml of cell suspension to about 50 ng/ml. In further embodiments, the concentration of TGF-β used in compositions of the invention ranges from about 5 pg/ml to about 40 ng/ml, from about 10 pg/ml to about 30 pg/ml, from about 20 pg/ml to about 20 ng/ml, from about 30 pg/ml to about 10 ng/ml, from about 50 pg/ml to about 1 ng/ml, from about 60 pg/ml to about 500 pg/ml, from about 70 pg/ml to about 300 pg/ml, from about 80 pg/ml to about 200 pg/ml, and from about 90 pg/ml to about 100 pg/ml. In further embodiments, the concentration of TGF-β used is determined based upon endpoints such as percentage of FOXP3+ cells produced in a population of cells and stability of FOXP3 expression. Such endpoints can be determined using methods known in the art and described herein.

IL-2 can be any form of IL-2 that is active on the mammalian cells being treated. For human cells, recombinant IL-2 is generally used. Recombinant human IL-2 can be purchased from R & D Systems (Minneapolis, Minn.). In general, the concentration of IL-2 used ranges from about 1 Unit/ml of cell suspension to about 300 U/ml. In further embodiments, the concentration of IL-2 ranges from about 1 U/ml to about 275 U/ml, from about 2 U/ml to about 250 U/ml, from about 3 U/ml to about 225 U/ml, from about 4 U/ml to about 200 U/ml, from about 5 U/ml to about 180 U/ml, from about 10 U/ml to about 170 U/ml, from about 15 U/ml to about 160 U/ml, from about 20 U/ml to about 150 U/ml, from about 25 U/ml to about 140 U/ml, from about 30 U/ml to about 130 U/ml, from about 35 U/ml to about 120 U/ml, from about 40 U/ml to about 110 U/ml, from about 45 U/ml to about 100 U/ml, from about 50 U/ml to about 90 U/ml, from about 55 U/ml to about 800 U/ml and from about 60 U/ml to about 70 U/ml.

In still further aspects, compositions of the invention for treating nTregs include one or more T cell activators. Such T cell activators include any agent capable of stimulating T cells. T cell activators may include in some exemplary embodiments anti-CD2, including anti-CD2 antibodies and the CD2 ligand, anti-CD3, anti-CD28, LFA-3, Concanavalin A (Con A), and staphylococcus enterotoxin B (SEB). In some embodiments, T cell activators are used in concentrations from about 0.1 to about 5.0 μg/ml. In further embodiments, concentrations of T cell activators range from about 0.2 to about 4.0, about 0.3 to about 3.0, about 0.4 to about 2.0, and about 0.5 to about 1.0 μg/ml. In many embodiments, anti-CD3 and anti-CD28 are used alone or in combination with TGF-β. In further embodiments, one or more other cytokines are used in combination with agents such as atRA as well as T cell activators such as anti-CD3 and anti-CD28. In general, as used herein unless otherwise indicated, to "stimulate" T cells means to contact the cells with one or more T cell activators, including without limitation anti-CD3 and anti-CD28. The anti-CD3 and/or the anti-CD28 may be soluble or immobilized on a support such as a bead. Stimulation of nTregs with T cell activators may be in the presence of a regulatory composition comprising a vitamin A derivative such as atRA alone or in combination with one or more other agents including without limitation trichostatin A and azacytidine, or such stimulation may occur prior to or subsequent to contact of the T cells with a regulatory composition for expansion and stabilization of phenotype of nTregs.

In some aspects, regulatory compositions of the invention will further include in addition to a vitamin A derivative such as atRA agents that accelerate differentiation of T cells into suppressor cells. Such agents can include without limitation active metabolites of retinoic acid, synthetic retinoids, and histone deacetylase inhibitors such as trichostatin A or valproic acid, or peroxisome proliferator receptor-gamma (ppAR-gamma) agonists such as rosiglitazone. Such agents may be used with one or more other agents in regulatory compositions of the invention, including without limitation cytokines, T cell activators, trichostatin A, and agents that affect the methylation of transcription factors, such as azacytidine.

In some embodiments, regulatory compositions of the invention comprise only a vitamin A derivative such as atRA. In further embodiments, regulatory compositions comprising a vitamin A derivative such as atRA further include only one other agent such as a TGF-β, azacytidine, trichostatin A, or a T cell activator. In other embodiments, combinations of multiple agents in addition to a vitamin A derivative are included in regulatory compositions of the invention and used to treat nTregs to expand the numbers of nTregs and stabilize their phenotype. In still further embodiments, regulatory compositions comprising a vitamin A derivative alone or in combination with one or more agents described herein further include buffers, salts, and/or pharmaceutically acceptable carriers to treat nTregs to expand the population and stabilize phenotype.

In some embodiments, a regulatory composition for treating nTregs is contacted with the cells at the initiation of a cell culture, and in some situations a regulatory composition is contacted with the cells at least once after initiation of the cell culture. In some situations a regulatory composition is contacted with the cells at the initiation of the cell culture and then again at least once after initiation of the cell culture.

In some embodiments, one or more components of a regulatory composition are added to a culture of nTregs at least once after initiation of the culture. In further embodiments, one or more components of a regulatory composition are added to a culture of cells from about 2 to about 15 times during the lifetime of the culture. In still further embodiments, one or more components of a regulatory composition are added to a culture of cells from about 3 to about 14, about 4 to about 13, about 5 to about 12, about 6 to about 11, about 7 to about 10, and about 8 to about 9 times during the lifetime of a culture. In some embodiments, these cultures may also include cells other than T cells. In other embodiments, these cultures are enriched for nTregs and other kinds of cells are removed from the culture. In further embodiments, non-nTreg cells are removed before the start of a culture or during the lifetime of the culture. In still further embodiments, non-nTreg cells are removed using cell sorting methods known in the art.

In some embodiments, prior to treatment with a regulatory composition and prior to stimulation with a T cell activator, the nTregs are "primed" with one or more agents. By "primed" is meant that the non-regulatory T cells are contacted with the one or more agents prior to contact with the regulatory composition. For example, the cells may be contacted with azacytidine, retinoic acid (including atRA), trichostatin A, TGF-β, IL-2 or some combination thereof prior to initiation of cell culture and/or prior to contact with a regulatory composition comprising a vitamin A derivative such as atRA alone or in combination with one or more of the agents used to prime the cells. In an exemplary embodiment, cultures of nTregs are primed with TGF-β and IL-2, stimulated with a T cell activator in the presence of a composition comprising an agent that comprises atRA, an agent that affects the methylation of FOXP3, an agent that affects the differentiation of cells into suppressor cells, an agent that is a histone deacetylase inhibitor, or some combination of these and/or other agents. In still further embodiments, the regulatory composition also includes TGF-β and/or IL-2.

In some embodiments, components of regulatory compositions for treating nTregs include components known in the art for generating induced regulatory T cells (iTregs) from non-regulatory T cells. Such components are described in for example U.S. Pat. Nos., 6,228,359; 6,358,506; 6,797,267; 6,803,036; 7,381,563 and 6,447,765, and U.S. application Ser. Nos. 10/772,768; 11/929,254; 11/400,950; 11/394,761;

and 12/421,941, all of which are hereby incorporated in their entirety for all purposes and in particular for all teachings (including written description, figures, and working examples) directed to methods and compositions for generating induced regulatory T cells from non-regulatory T cells. Such methods and compositions can in some embodiments also be applied to expand and stabilize the phenotype of nTregs.

In one aspect, the present invention provides methods for generating therapeutic numbers of nTregs within about seven to about ten days. By "therapeutic numbers" is a number of cells that can be administered to a patient to alleviate or prevent an immune disorder, including an autoimmune disease. In a further aspect, methods for generating therapeutic numbers of nTregs include treating nTregs isolated from a patient. By "treating" herein is meant that the cells are contacted with a regulatory composition comprising components described herein that expand nTreg numbers and stabilize their phenotype. In an exemplary embodiment, treating the cells includes incubating the cells with the regulatory composition (for example by adding regulatory composition to the cell culture medium) for a time period sufficient to expand the cells and stabilize their phenotype. The incubation is generally conducted under physiological temperature.

A cell culture of nTregs treated in accordance with the methods and compositions described herein may be maintained for purposes of the present invention for about 2 days to about 3 months, for about 3 days to about 2 months, for about 4 days to about 1 month, for about 5 days to about 20 days, for about 6 days to about 15 days, for about 7 days to about 10 days, and for about 8 days to about 9 days.

In certain embodiments, a sample containing nTregs is submitted to flow cytometry methods to enrich the population for FOXP3+ cells. Such methods may be applied prior to and/or subsequent to the treatment methods described herein for expanding and stabilizing the nTreg population. In further embodiments, such flow cytometry methods are in accordance with methods described in Zhou et al., (2010), *J. Molecular and Cell Biology*, 2:164-169, which is hereby incorporated by reference in its entirety for all purposes.

In further embodiments, viable FOXP3$^+$ cells can be isolated or enriched based on forward scatter (FSC) and side scatter (SSC) properties as herein disclosed. Flow cytometric analysis is performed by applying laser beam(s) with a single wavelength to a fluid containing cells and then capturing the light transmitted from the fluid using a plurality of detectors. The FSC signal is the signal detected in line with, or at low angles away from, the direction of the laser beam, while the SSC signal is detected at greater angles away from the direction of the laser beam. nTregs can be expanded in vitro over the course of 1, 2, 3, 4, 5, 6, 7, or more days by the addition of anti-CD3/CD28 coated beads and IL-2 to the culture medium. Analysis of these cultured cells by flow cytometric reveals a distinctive dot plot profile as shown in Zhou et al. Surprisingly, the highest percentage of cells expressing FOXP3$^+$ are those cells with relatively high FSC and low SSC. Such cells are referred to as the lymphoblast cell population. The lymphoblast population is the 80%, 75%, 70%, 65%, 60%, 55%, 50%, 45%, 40%, 35%, 30%, 20%, 15%, 10% of cells identified as having high FSC. Among the lymphoblast population, 75%, 80%, 85%, 90%, 95%, 99% of these cells express FOXP3.

Additionally, the lymphoblast population possessed relatively low SSC. For example, lymphoblast cells are among the 50%, 45%, 40%, 35%, 30%, 25%, 20%, 15%, 10%, 5%, or less of cells with the lowest SSC.

Accordingly, the FSC and SSC properties of a cell can be used to identify and enrich for those cells which express FOXP3$^+$ A number of factors may influence the FSC profile of a cell or a population of cell; these include differences in size, in refractive index between the cells and the suspending medium, the cell's internal structure, and the presence within or upon cells material with strong absorption at the illumination wavelength used. However, one of skill is aware of and can compensate for these limitations when using FSC and SSC properties in identifying a particular cell or cell population. Such methods include, without limitations, those disclosed in U.S. Pat. No. 5,084,394, incorporated by reference in its entirety herein.

III. Use of Treated nTregs

The present invention encompasses populations of nTregs expanded and stabilized using methods and compositions described herein. These treated nTregs can be used in therapeutic and research applications. As discussed above, treated nTregs are nTregs that have been expanded and stabilized in accordance with the present invention such that they are resistant to Th17 conversion and maintain suppressive activities in the presence of components of inflammatory infiltrates such as IL-6.

In an exemplary aspect, nTregs treated in accordance with methods and compositions of the invention are used to treat an inflammatory response in a patient. In a specific example, nTregs are isolated from a patient suffering from an inflammatory response. These isolated nTregs are treated in culture using in accordance with the methods described herein. In a specific embodiment, the nTregs are treated with atRA alone or in combination with one or more of any of the other agents discussed herein to expand the number of nTregs and stabilize their phenotype. These treated, expanded and stabilized Tregs are then administered to the patient.

In one aspect, treated nTregs described herein are administered to patients suffering from, for example, immune disorders, including autoimmune diseases. In a further aspect, treated nTregs described herein can be used to prevent or treat allograft rejection.

nTregs of the invention can be administered to patients using methods generally known in the art. Such methods include without limitation injecting or introducing the treated nTregs into a patient. In some embodiments, nTregs are introduced into a patient via intravenous administration. In further embodiments, additional reagents such as buffers, salts or other pharmaceutically acceptable additives may be administered in combination with nTregs. In still further embodiments, treated nTregs of the invention are administered in combination with atRA. In other embodiments, treated nTregs of the invention are generated using atRA, and these treated nTregs are then administered to a patient in the absence of atRA. In still further embodiments, atRA that may be present in the culture of nTregs after treatment for expansion and stabilization of phenotype is removed prior to administration of the treated nTregs to the patient.

After introducing the cells into the patient, the effect of the treatment may be evaluated using methods known in the art. Examples of such evaluations can include without limitation: measuring titers of total Ig or of specific immunoglobulins, renal function tests, tissue damage evaluation, and the like.

Treatment using nTregs of the invention may be repeated as needed or required. For example, the treatment may be done once a week for a period of weeks, or multiple times a week for a period of time, for example 3-5 times over a two week period. Over time, the patient may experience a relapse of symptoms, at which point the treatments may be repeated.

In one exemplary aspect, the invention provides a method of treating an aberrant immune response or an autoimmune disease in a patient, and this method includes the step of administering treated nTregs to the patient. In this aspect, the treated nTregs were expanded and stabilized by treatment of a culture of nTregs with a regulatory composition comprising a vitamin A derivative such as atRA alone or in combination with one or more additional agent including without limitation: azacytidine, trichostatin A, TGF-β, IL-2, a T cell activator such as anti-CD3 and anti-CD28, or any combination of agents described herein and known in the art.

IV. Compositions Comprising Treated nTregs

The present invention encompasses populations of treated nTregs expanded and stabilized in accordance with methods described herein. Such treated nTregs can be included in compositions that further comprise pharmaceutically acceptable carriers.

The present invention also encompasses regulatory compositions that include vitamin A derivatives alone or in combination with other agents. Regulatory compositions of the invention can in some embodiments further include azacytidine, a histone deacetylase inhibitor, ppAR-gamma agonist, trichostatin A, TGF-β, IL-2, anti-CD3, anti-CD28, and any combination thereof. These regulatory compositions may in some situations be combined with cell culture media. In further embodiments, the present invention also encompasses regulatory compositions of the invention in combination with nTregs.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Cell Purification, In Vitro Cell Stimulation and Suppressor Assay nTreg cells were sorted from thymus of DBA/1 or Foxp3$^{gfp}$ knock-in DBA/1 mice by gating on CD4$^+$CD25$^+$ or CD4$^+$ GFP$^+$ cells. Cell populations were sorted to >99% purity.

To activate nTregs, CD25$^+$ or GFP$^+$ cells were stimulated with anti-CD3/CD28 coated beads (1:5, one bead to five cells), rmIL-2 (100 U/ml) (R&D) with DMSO or all-trans retinoic acid (atRA, 0.05 µM) for 3 days. To generate Th17 cells, these activated nTregs were stimulated with immobilized anti-CD3 (1 µg/ml), soluble anti-CD28 (1 µg/ml), anti-IL-4 (10 µg/ml) (BD biosciences), anti-IFN-γ and IL-6 (10 ng/ml) (BD Pharmingen) for 3 days.

To measure suppressive activities, responder T cells were stimulated with soluble anti-CD3 (0.025 µg/ml) and irradiated APC (1:1), nTregs pretreated with at-RA or without atRA were added to cultures at a ratio of 1:4 (one nTreg to four responder cells). After 72-hour cultures, triplicate wells were pulsed with 1 µCi of [$^3$H]-TdR for the final 16 hours. Cell proliferation was determined by [$^3$H]-TdR incorporation using scintillation counting.

Example 2

Figure 1B:
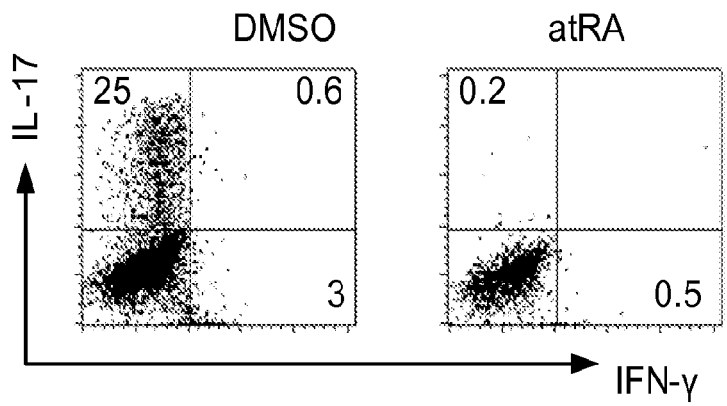
FIG. 1 shows data on effect of addition of atRA to nTregs on conversion to Th17 cells.
FIG. 1C shows soluble IL-17A in cultures of CD4+CD25+ cells stimulated with anti-CD3 and anti-CD28 and IL-6 with or without atRA.
FIG. 1D shows the percentage of FOXP3 expressing cells resulting from treatment of nTregs activated with anti-CD3/CD28 in the presence of atRA or DMSO with or without IL-6.
FIG. 1E shows suppressive activities of nTregs in presence of IL-6 and/or atRA determined by inhibition of tritiated thymidine uptake.
Figure 1C:
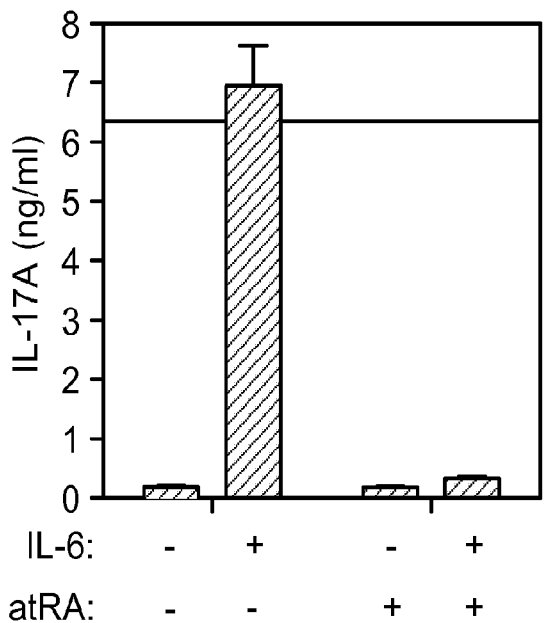

Treatment of nTregs with atRA Stabilizes Phenotype by Rendering nTregs Resistant to Th17 Conversion and Sustaining FOXP3 Expression Naive CD4$^+$CD25$^+$CD62L$^+$ nTregs sorted from the thymus of DBA/1 mice were stimulated with anti-CD3/CD28 antibodies with or without IL-6. nTregs TCR activated with IL-6 have been shown to become Th17 cells. FIG. 1A-C show, however, that when atRA was added to cultures containing IL-6 both intracellular IL-17 and soluble IL-17 production was completely blocked. Because atRA was dissolved in DMSO, similar volumes of DMSO was added to the cultures to exclude the possibility that atRA has a non-specific toxic effect on T cells (FIGS. 1A and B). For the data in FIGS. 1A and B, CD4$^+$CD25$^+$ cells were stimulated with immobilized anti-CD3 (1 µg/ml), soluble anti-CD28 (1 µg/ml) and IL-6 (10 ng/ml) with or without atRA (0.05 µM). 3 days later, these cells were restimulated with PMA (0.25 µg/ml) and ionomycin (0.25 µg/ml) for 5 h and brefeldin A (5 µg/ml) for 4 h, and then collected for intracellular IL-17 and IFN-γ staining. Values indicate mean±SEM of four separate experiments and representative of these experiments Addition of atRA did not affect the activation and proliferation status of nTregs, suggesting that atRA may specifically inhibit Th17 cell conversion from IL-6-treated nTregs. Thus, atRA enabled nTregs to become resistant to Th17 conversion.

Figure 1D:
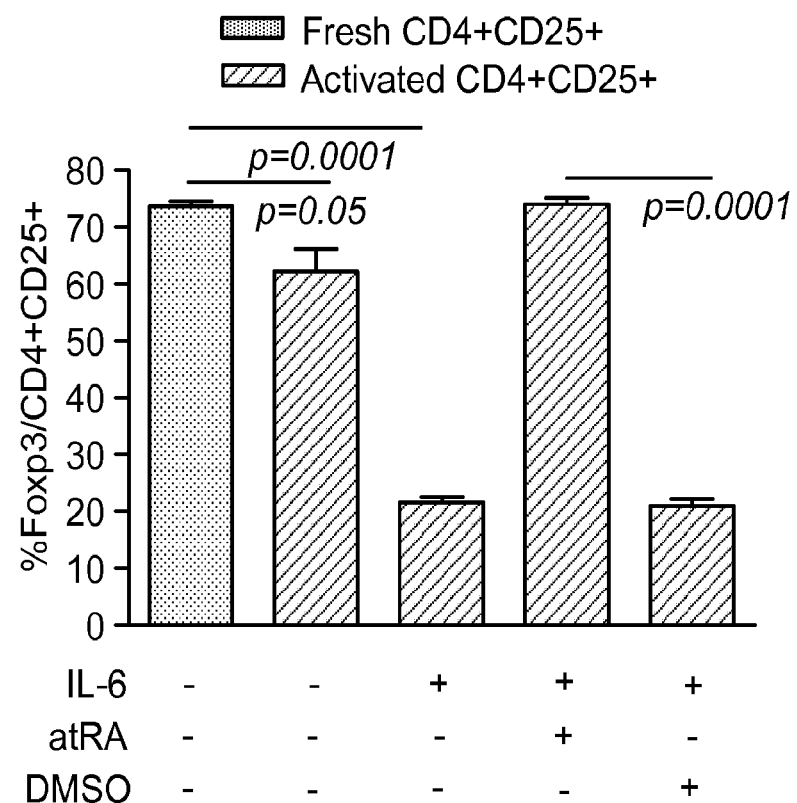

While nTreg cells stimulated with anti-CD3/CD28 antibodies without IL-2 for 4 days ex vivo slightly decreased FOXP3 expression, addition of exogenous IL-6 markedly decreased FOXP3 expression (FIG. 1D). Interestingly, the addition of atRA to nTregs in the presence of IL-6 almost completely prevented the down-regulation of the FOXP3 expression seen in control (DMSO) cultures (FIG. 1D). For the experiments in FIG. 1D, nTregs were activated with anti-CD3/CD28 coated beads in the presence of the atRA solvent (DMSO) or atRA (0.05 µM) with or without IL-6 (10 ng/ml) for 3 days and Foxp3 expression was determined and compared to freshly isolated CD4$^+$CD25$^+$ cells by FACS intracellular staining.

Figure 1E:
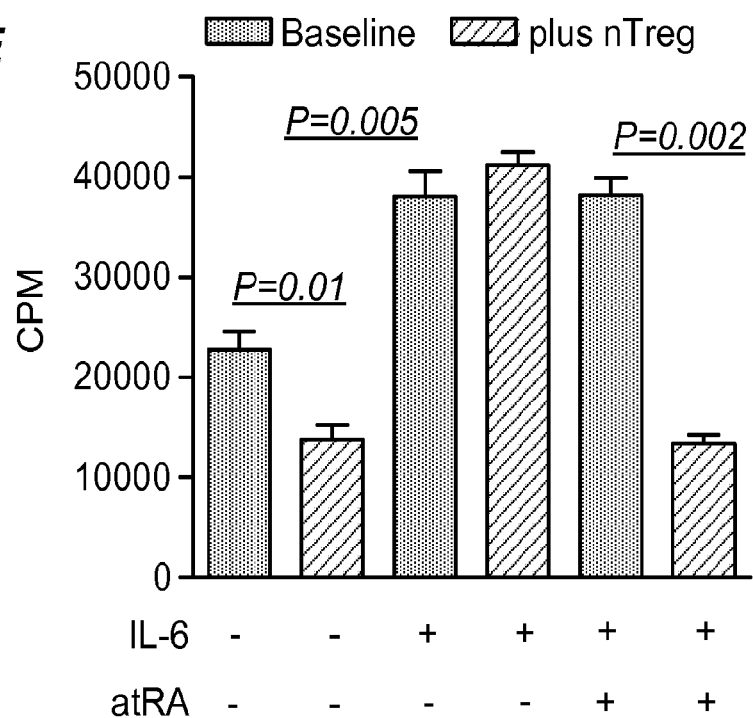

IL-6 also markedly decreases the suppressive activities by nTreg cells (FIG. 1E). The suppressive activity of nTregs against T responder cell proliferation was completely abolished in the presence of IL-6. Conversely, addition of atRA to the cultures blocked this effect of IL-6 and maintained the suppressive activity of nTregs. In addition, addition of atRA alone did not suppress T cell response in the presence of IL-6 but in the absence of nTregs (FIG. 1E), suggesting that atRA does not directly interfere with the role of IL-6 in immune response of T responder cells. Taken together, these data show that atRA can overcome the pro-inflammatory effects of IL-6 and sustain the stability and suppressive function of nTreg cells. Values indicate the mean±SEM of four independent experiments for FIGS. 1D and E. The p values were calculated by Student's test and indicate significant differences between cultures with or without atRA (P<0.05).

In FIG. 1C, soluble IL-17A in the culture supernatants was analyzed by an ELISA. The horizontal line indicates the levels of IL-17A in the supernatant of naïve TCR-stimulated CD4$^+$ cells in the presence of IL-6 and TGF-β. E, the suppressive activities of nTregs in the presence of IL-6 and/or atRA were determined by the inhibition of tritiated thymidine ([$^3$H]-TdR) uptake.

Figure 2A:
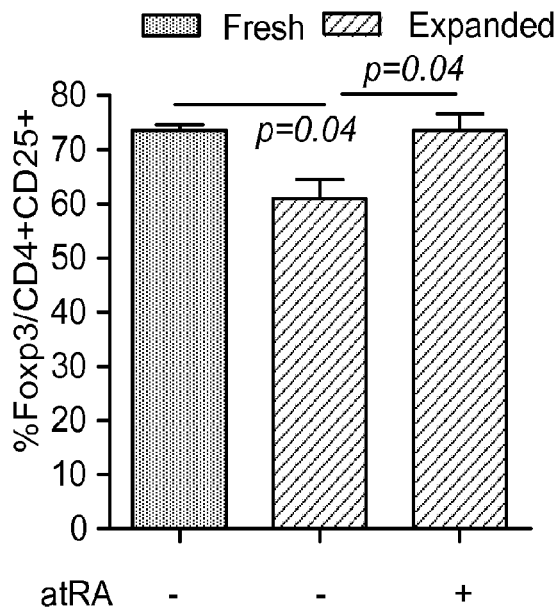
FIG. 2A shows the percentage of FOXP3 cells in fresh and expanded nTregs with and without atRA.
Figure 2B:
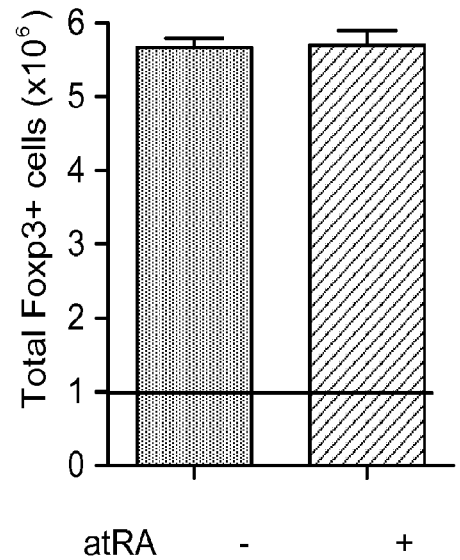
FIG. 2B shows the total number of FOXP3 cells in fresh and expanded nTregs with and without atRA.
Figure 2C:
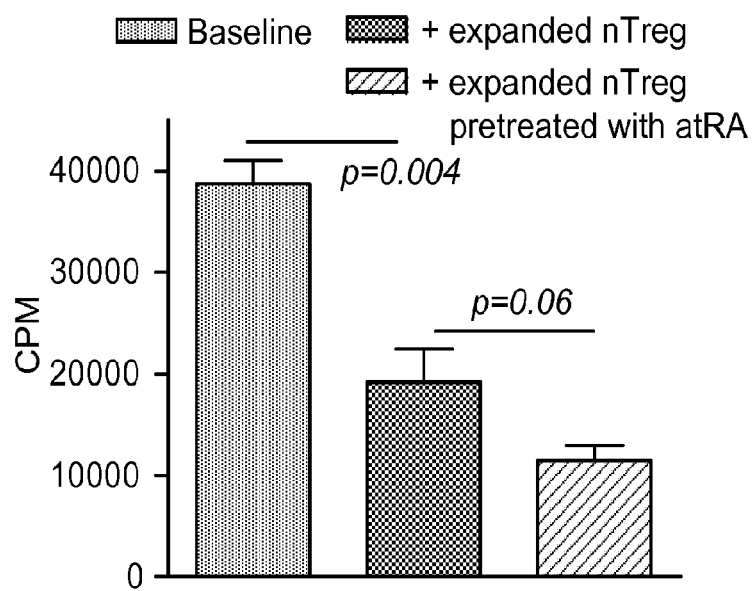
FIG. 2C shows suppressive activity of nTregs with or without atRA treatment.

Example 3 nTregs Expanded with atRA are Resistant to the Inhibitory Effects of IL-6 on nTregs and Prevent Th17 Conversion Natural Tregs expanded ten-fold in one week after stimulation with anti-CD3/28 coated beads with IL-2 and addition of atRA to the culture slightly decreased the expansion of nTregs (eight-fold). Unlike nTregs expanded with IL-2 only where FOXP3 expression gradually decreased, FOXP3 expressed by nTregs expanded with atRA remained stable and the suppressive activities of these cells were even superior than nTregs expanded without atRA (FIGS. 2A and B), which is consistent with reports that suppressive activity of Treg cells is closely associated with the expressive levels of FOXP3. For the data in FIGS. 2A and B, $CD4^+CD25^+$ cells were stimulated with anti-CD3/CD28 coated beads (1:5), rmIL-2 (100 U/ml) with DMSO or atRA (0.05 µM) for 7 days and the FOXP3 expression (A) and total $Foxp3^+$ cell numbers (B) were determined.

Figure 2D:
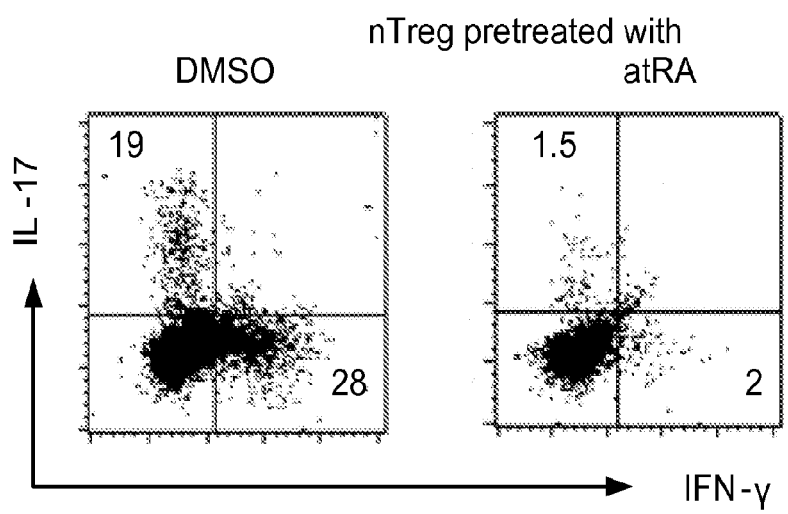
FIG. 2D shows IL-17 expression in nTregs pretreated with DMSO or atRA.
Figure 2E:
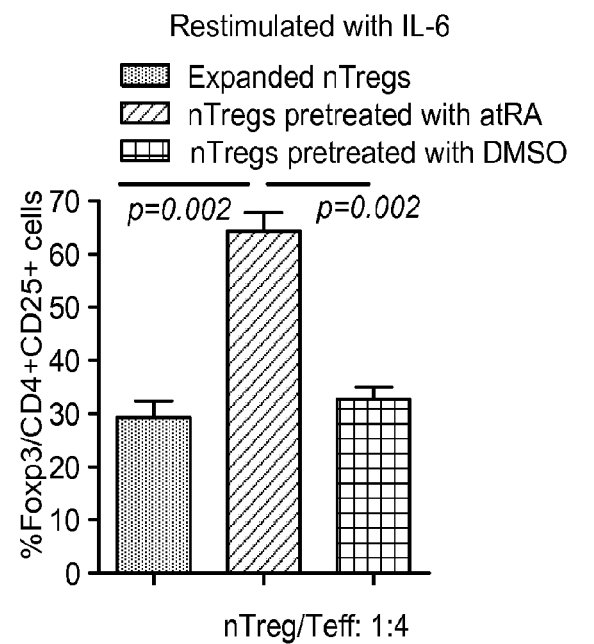
FIG. 2E shows percentage of FOXP3 expression in nTregs treated with atRA or DMSO.

As shown in FIG. 2D, when nTregs expanded without atRA were restimulated with anti-CD3/28 beads with IL-6, between 20 to 30 percent of nTregs converted to Th17 or Th1. In contrast, nTregs expanded with atRA were completely resistant to Th17 and Th1 conversion FIG. 2D). For the experiments in FIG. 2D, $CD4^+CD25^+$ cells were activated as in FIG. 2A and re-stimulated with IL-6 as for the experiments in FIG. 1A described above. Intracellular IL-17 and IFN-γ expression was determined by FACS staining. Results are representative of three independent experiments. IL-17 and IFN-γ secreted into the supernatants was consistent with intracellular cytokine expression (data not shown). In addition, FOXP3 expression by nTregs expanded without atRA was markedly decreased following re-stimulation with IL-6, while nTregs previously treated with atRA maintained FOXP3 expression (FIG. 2E).

Figure 2F:
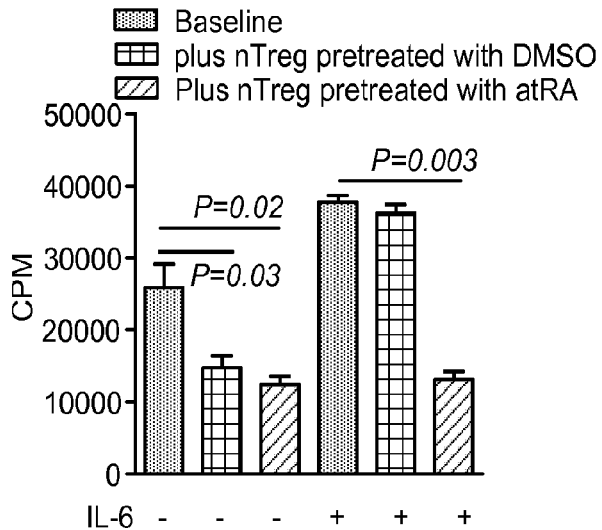
FIG. 2F shows suppressive activities of atRA or DMSO treated nTregs in the presence or absence of IL-6.

Besides maintaining FOXP3 expression, nTregs treated with atRA also retained the suppressive function in the presence of IL-6. FIG. 2F shows that nTregs expanded without atRA completely lost their suppressive activity following re-stimulation with IL-6. In sharp contrast, the suppressive function of nTregs expanded in the presence of atRA was completely intact when these cells were restimulated with IL-6 (FIG. 2E—values indicate the mean±SEM of three separate experiments). These nTregs were washed exhaustively after harvesting and atRA measured by HPLC in the supernatants in suppressive assay cultures was undetectable (data not shown). Thus, there was no carry over of atRA in the suppressive activity. These results show that treatment of nTregs with atRA can stabilize their phenotype and suppressive activity, and that continued presence of atRA is not necessary for their suppressive activity to be stabilized in an inflammatory milieu.

In FIG. 2F, the suppressive activities of atRA or DMSO treated nTregs in the absence or presence of IL-6 in vitro was determined by similar methods as in FIG. 1E. P values were calculated by Student's test and indicate significant differences between atRA and control treated nTregs (P<0.05).

Example 4 nTregs Treated with atRA can Ameliorate the Progression of Established Collagen-Induced Arthritis in Mice Since IL-6 is often a component of inflammatory infiltrates, the ability of atRA to stabilize nTregs in the presence of IL-6 offers the possibility that the transfer of atRA-treated nTregs can be therapeutic in established chronic immune-mediated diseases such as collagen-induced arthritis (CIA). Previous studies have indicated that the adoptive transfer of $CD4^+CD25^+$ nTreg cells can prevent the development of CIA, but their therapeutic effect on the established CIA in mice is unsatisfactory.

To test the effect of atRA-treated nTregs on collagen-induced arthritis in mice, DBA/1 mice were immunized with bovine collagen II in complete Freund's adjuvant (CII/CFA) and when the animals had developed arthritis at day 28 or earlier, $1 \times 10^6$ nTregs previously stimulated with or without atRA were transferred to the mice. Specific pathogen-free, female DBA/1 mice (6-8 weeks) were purchased from Jackson Laboratory. $Foxp3^{gfp}$ knock-in mice on the DBA/1 background were developed by backcrossing of $Foxp3^{gfp}$ knock-in mice on the C57BL/6 background to DBA/1 mice for 13 generations. All animals were treated according to National Institutes of Health guidelines for the use of experimental animals with the approval of the University of Southern California Committee for the Use and Care of Animals (Los Angeles, Calif.).

Figure 3A:
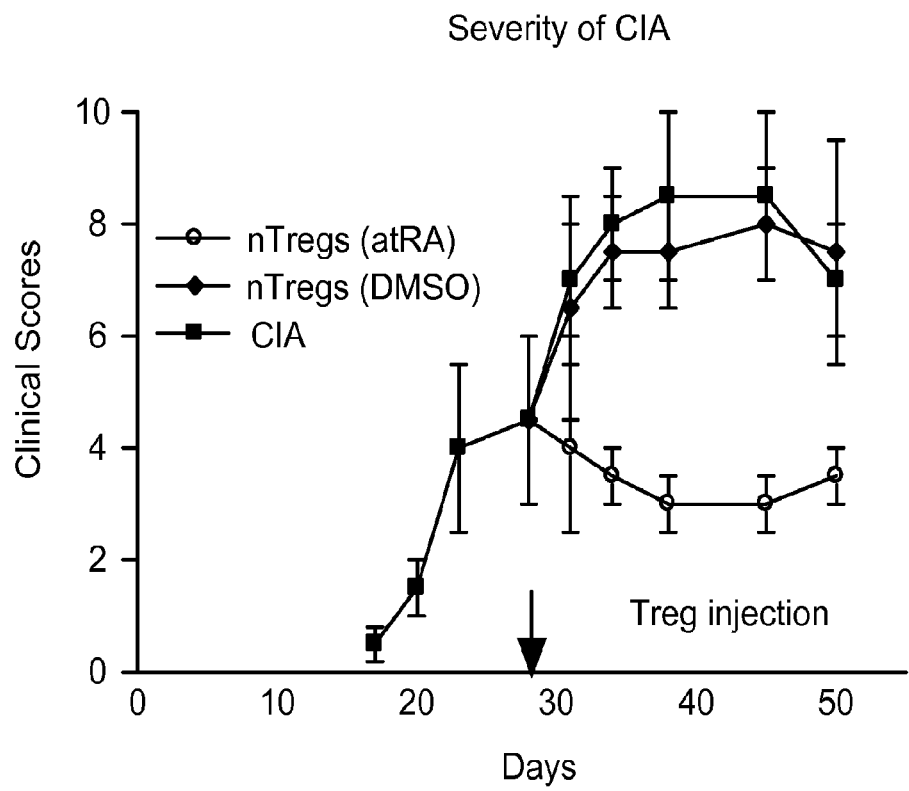
FIG. 3A shows clinical scores on the severity of collagen-induced arthritis in mice after treatment with DMSO or atRA treated nTregs.

As shown in FIG. 3A, transfer of atRA treated nTregs completely blocked the progression of arthritis symptoms, and could even decrease the clinical score compared to mice at day 28. Conversely, like control mice injected with only PBS, mice injected with nTregs activated without atRA developed increasingly more severe arthritis (FIG. 3A). For the experiments for FIG. 3A, nTregs were expanded with anti-CD3/CD28 coated beads (1:5) and IL-2 (100 U/ml) in the presence of DMSO or atRA (0.05 µM) for 4 days. Mice with established arthritis at day 28 after CII/CFA immunization were injected IV with $1 \times 10^6$ atRA treated nTregs, DMSO treated nTregs or PBS (control group). The mice were examined every three days after immunization and the clinical scores are indicated.

Figure 3B:
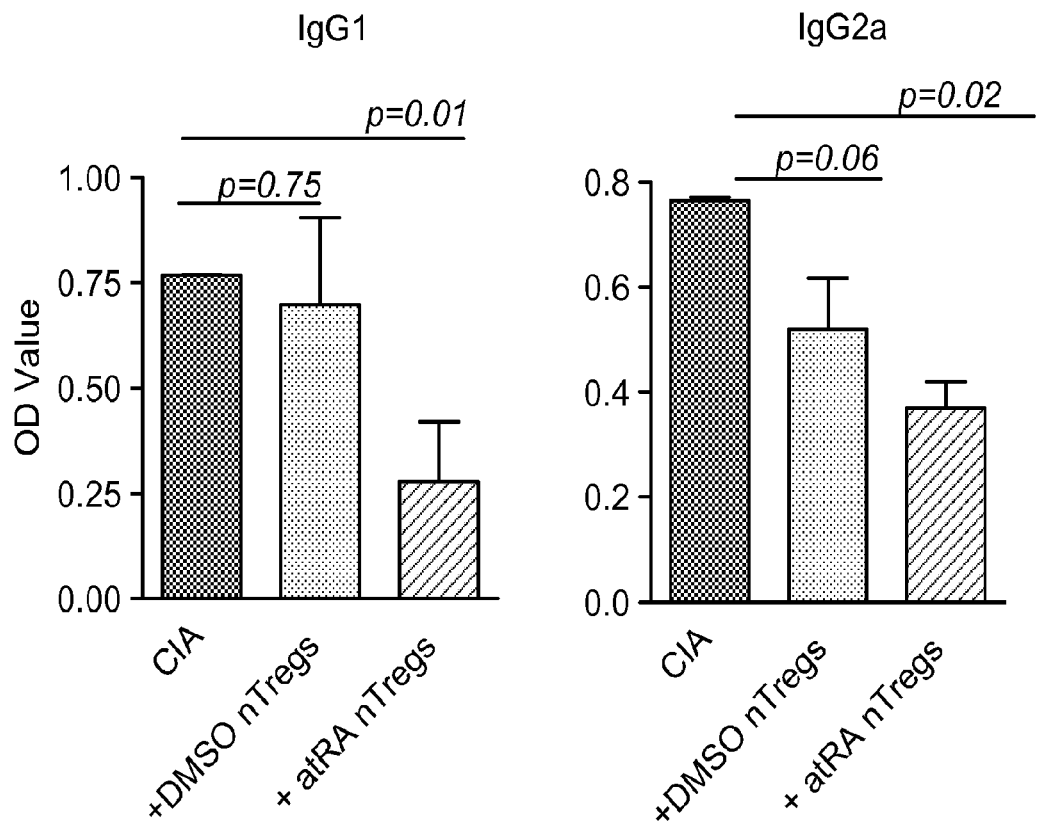
FIG. 3B shows IgG1 and IgG2a levels in sera on day 45 after treatment with DMSO or atRA treated nTregs.

In another experiment, $3 \times 10^6$ nTregs treated with or without atRA were administered to DBA/1 mice immunized with bovine collagen II, and the effects of these cells on CIA was similar to the effect in mice treated with $1 \times 10^6$ cells (data not shown). Thus, the absence of a protective effect of nTregs that were not treated with atRA could not be explained by insufficient cell numbers. The transfer of atRA-treated nTregs also suppressed the production of CII-specific antibodies in established CIA (FIG. 3B). This indicates that the clinical improvement is associated with a reduced CII-specific immune response. For the experiments in FIG. 3B, CII-specific IgG1 and IgG2a levels in sera on day 45 after CII/CFA immunization were measured by ELISA. Values indicate the mean±SEM of two independent experiments (n=8/group). The p values indicate significant differences between nTregs treated with atRA or solvent control (Student's t test, p<0.05).

Figure 4A:
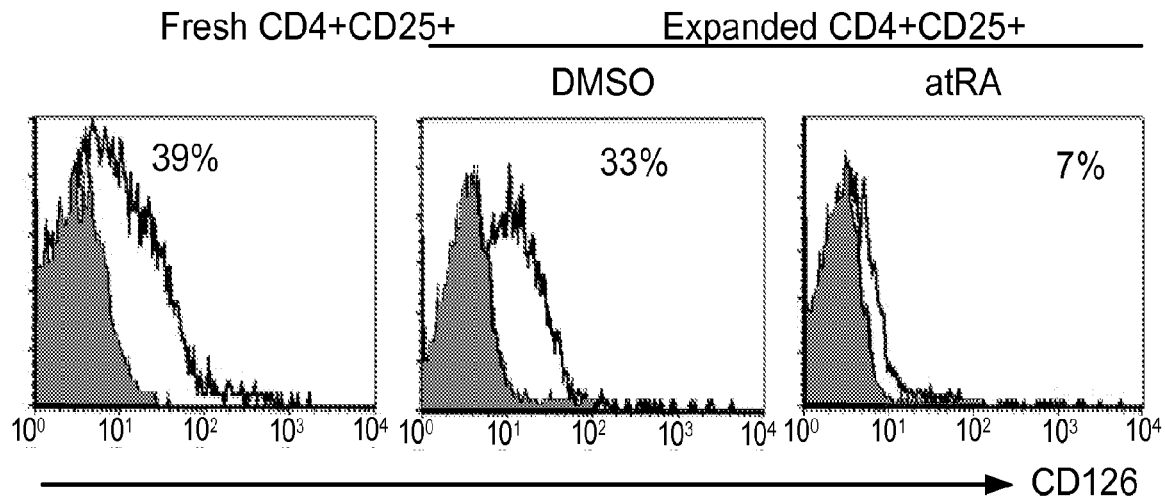
FIG. 4A shows data on CD126 expression in nTregs treated with or without atRA.
Figure 4B:
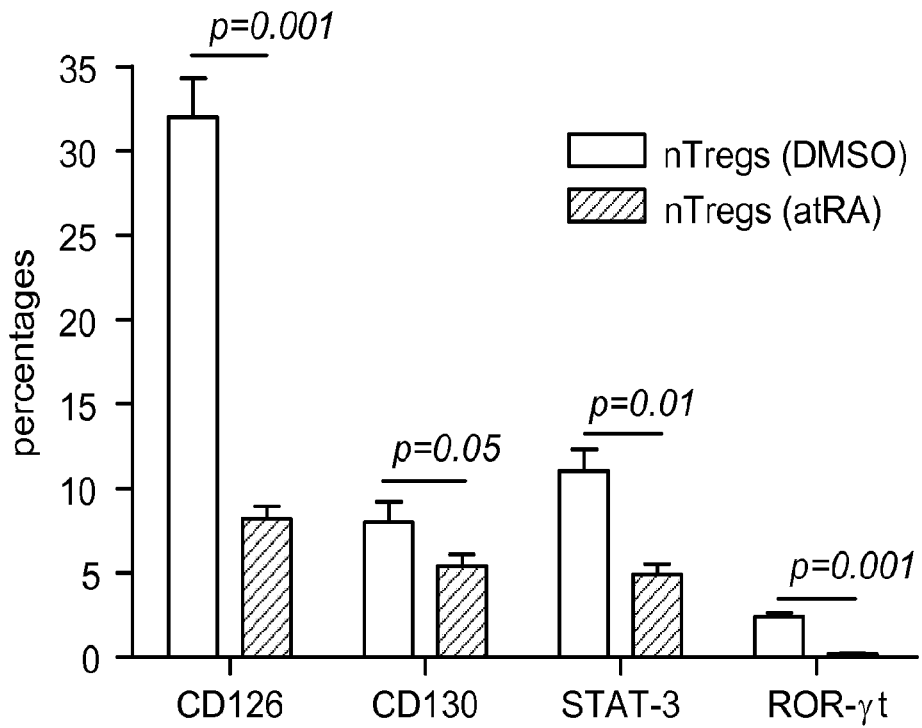
FIG. 4B shows percentage of CD126, CD130, STAT-3 and ROR-γt expression as determined by flow cytometry in nTregs treated with DMSO or atRA.

Example 5 nTregs Treated with atRA Maintain Phenotype and Function through Downregulation of IL-6 Receptor and Signaling It has been shown that atRA not only strongly inhibits the up-regulation of IL-6 Rα mRNA induced by TGF-β but also decreases the levels of p-Stat3 expression induced by IL-6 plus TGF-β. One potential mechanism by which atRA treatment stabilizes phenotype of nTregs, particularly suppressive function, may be through downregulation of the expression of IL-6R and IL-6R signaling. To investigate this potential mechanism, $CD4^+CD25^+$ cells were stimulated with anti- CD3/CD28 coated beads and IL-2 with or without atRA for 4 days. Similar to naive T cells, freshly isolated nTreg cells expressed substantial amounts of IL-6R α-chain (CD126) that slightly decreased after TCR activation (FIG. 4A). CD126 (IL-6Rα chain) expression was determined by flow cytometry. Interestingly, the addition of atRA markedly decreased the CD126 expression in activated nTregs (FIG. 4A). Although IL-6 Rβ (CD130) expression is not high by nTregs, addition of atRA also significantly decreased its expression (FIG. 4B). The IL-6 receptor expression reduction is likely associated with down-regulation of IL-6R signaling since addition of atRA also significantly decreased Stat-3 activation in nTregs (FIG. 4B). When atRA-treated nTregs were restimulated with IL-6, the decrease in IL-6 signaling was accompanied by a decrease of expression of ROR-γt (FIG. 4B), the crucial transcription factor required for Th17 cell differentiation. This finding is in agreement with reports that the combination of IL-2 and TGF-β has dramatic effects on both IL-6 receptor expression and signaling on nTreg cells. FIG. 4B shows the mean±SEM of surface CD126, CD130 (IL-6Rβ chain), intracellular phosphorylated STAT3 and transcription factor ROR-γt expression as determined by flow cytometry (n=4). The p values indicate significant differences between DMSO treated and atRA treated nTregs (p<0.05, t test).

Example 6

Effects of atRA Treatment in Human nTregs

Figure 5:
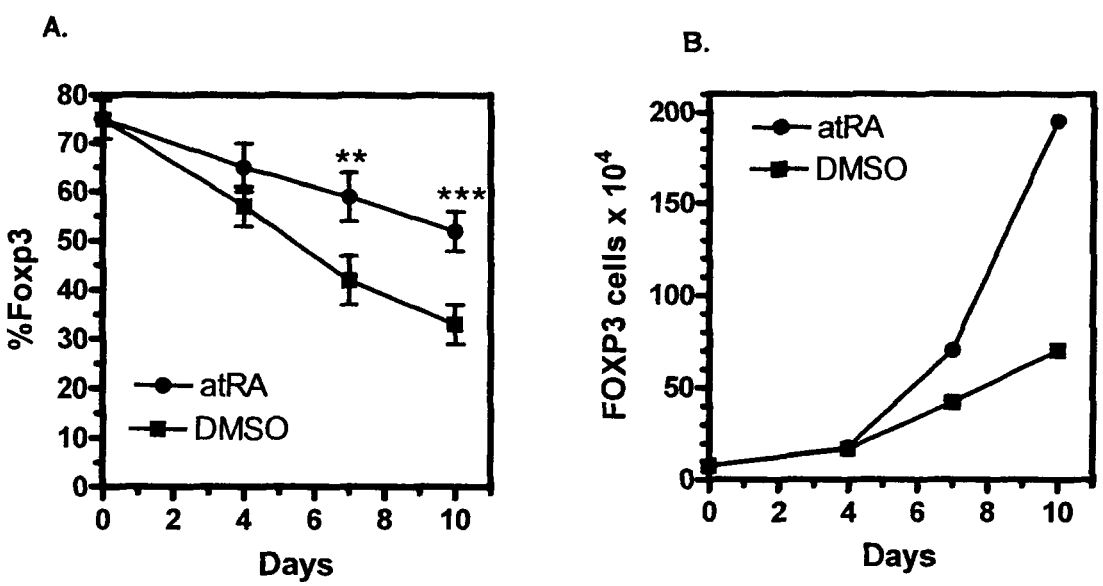
FIG. 5 shows data on the effect of atRA treatment on the expression of FOXP3 in human nTregs.
Figure 6A:
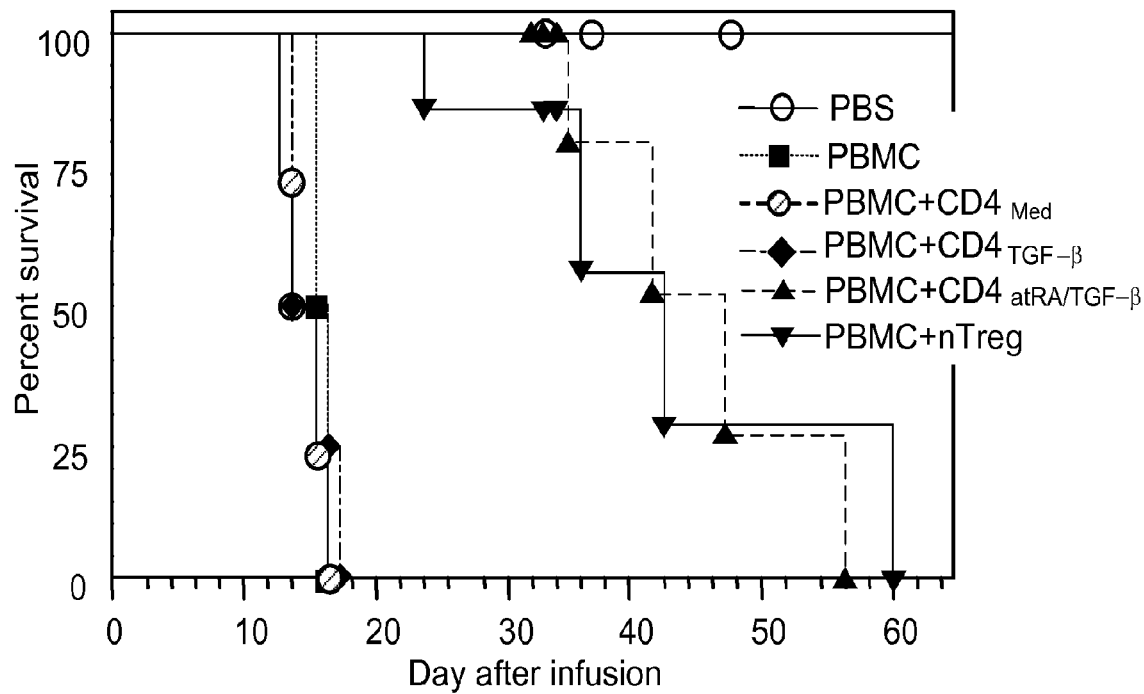
FIG. 6A shows that immuno-deficient NOD SCID IL-2R gamma chain deficient mice injected with human blood mononuclear cells died rapidly from human T cell-induced graft versus host disease.
Figure 6B:
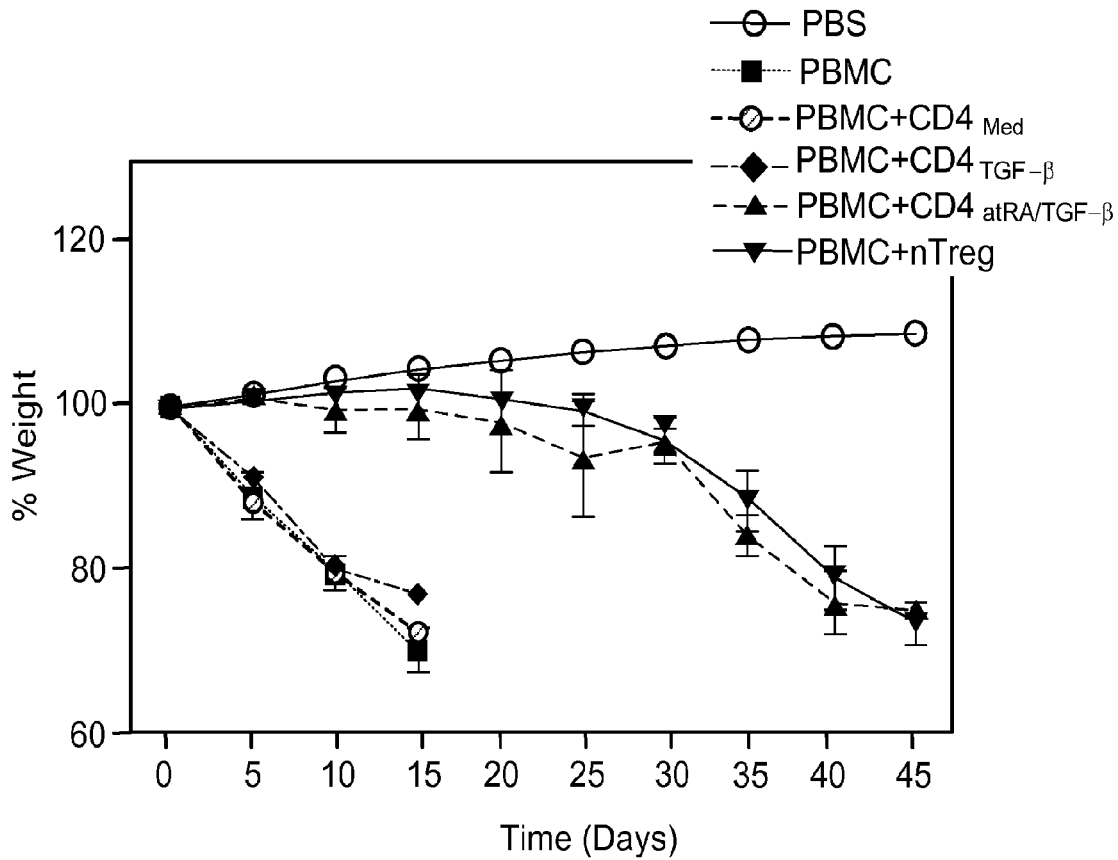
FIG. 6B shows that these mice lost weight and FIG. 6C shows that these mice had large amounts of human IgG antibody in their serum one week after injection with the human cells.
Figure 6C:
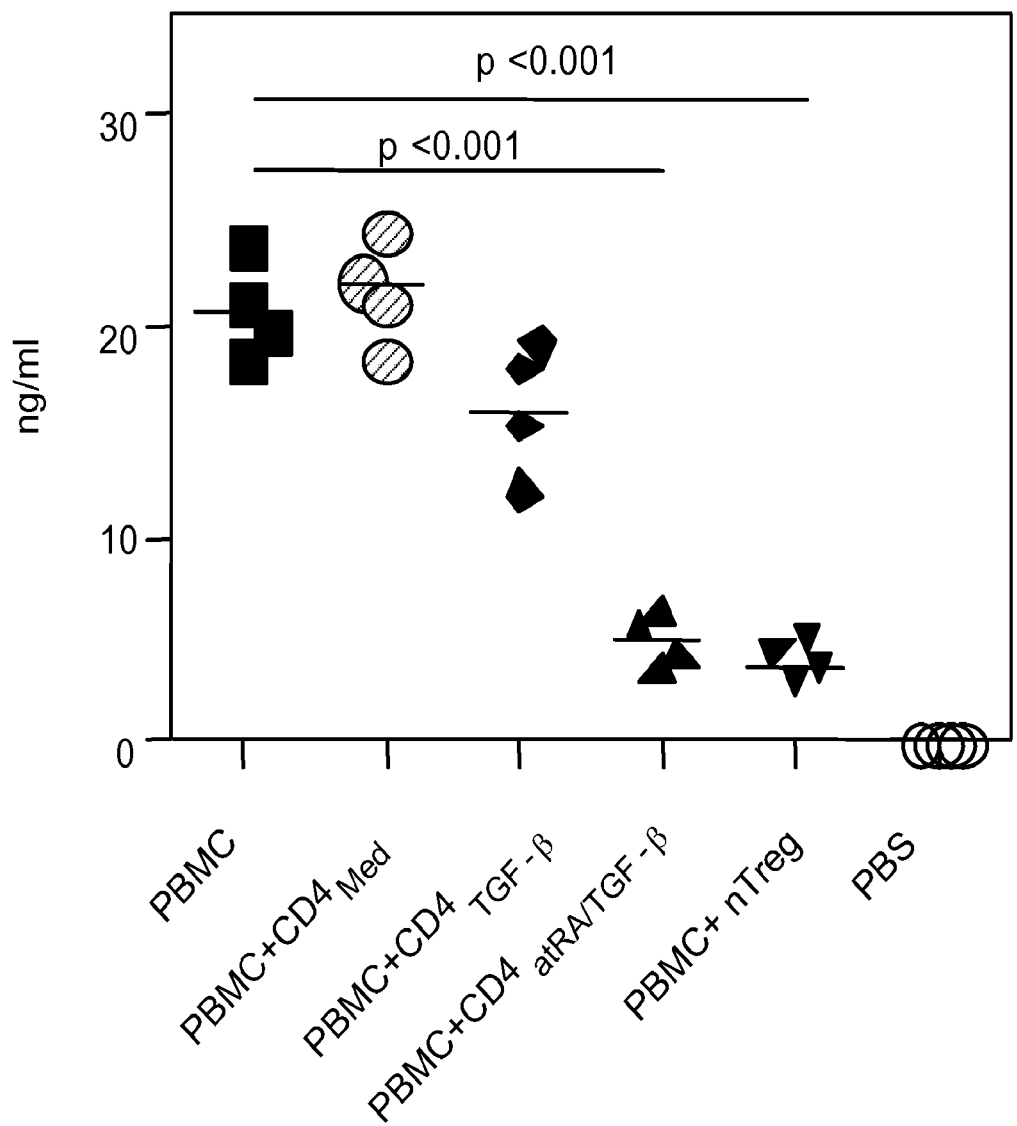
Figure 6D:
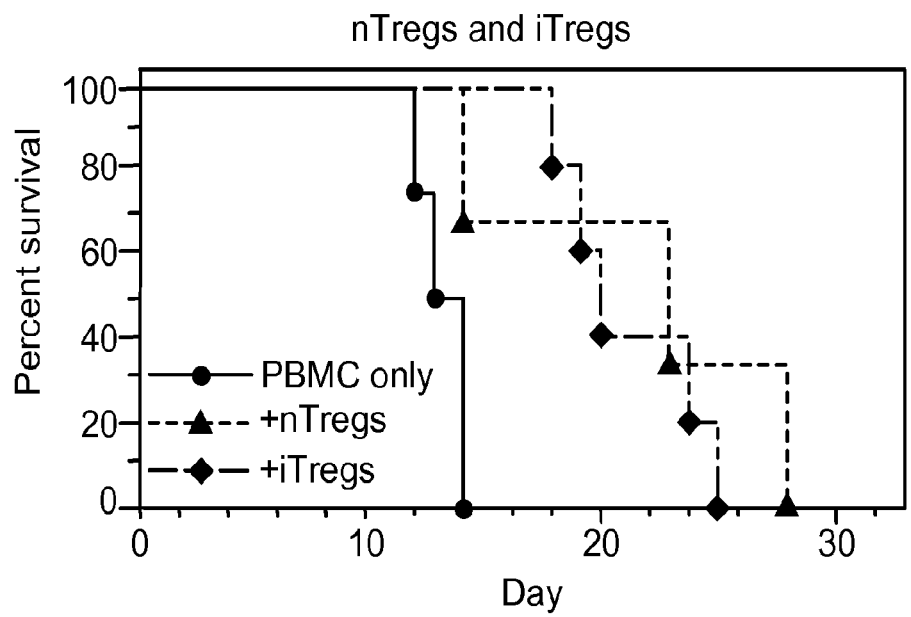
FIG. 6D shows that mice injected with nTregs and induced Tregs treated with all-trans retinoic acid (atRA) show increased survival in comparison to mice injected with human blood mononuclear cells.
Figure 6E:
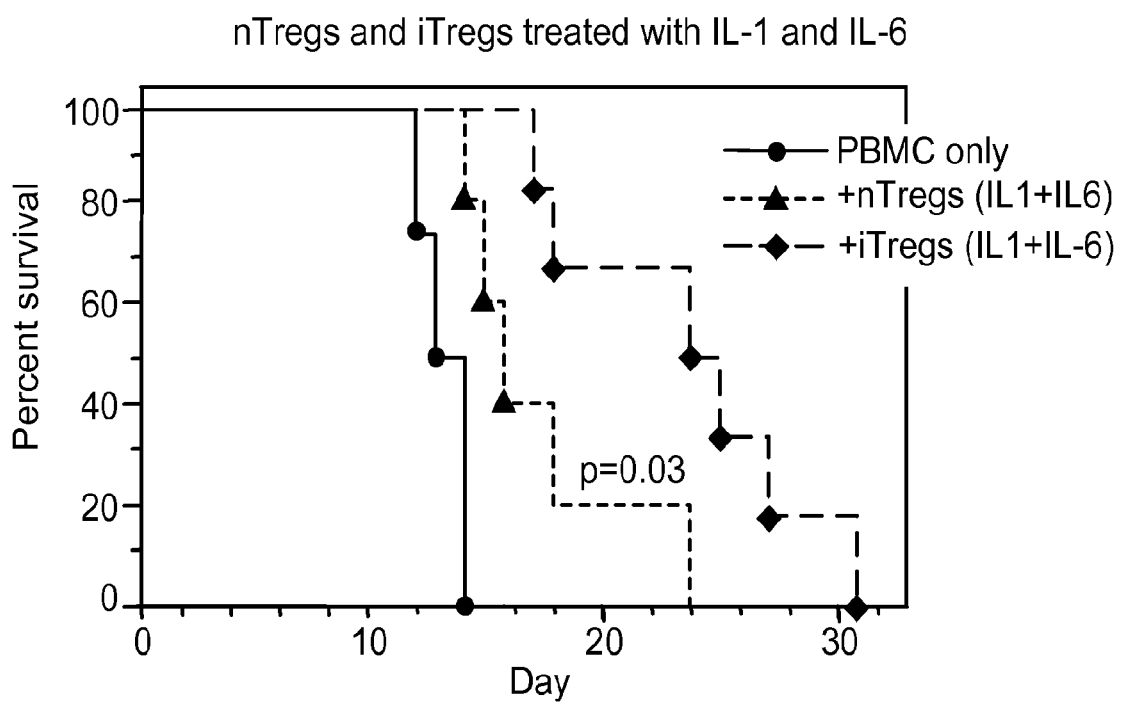
FIGS. 6E-G shows that mice injected with induced Tregs treated with atRA are more resistant to inflammatory cytokines IL-1 and IL-6 than mice injected with untreated nTregs or human blood mononuclear cells.
Figure 6F:
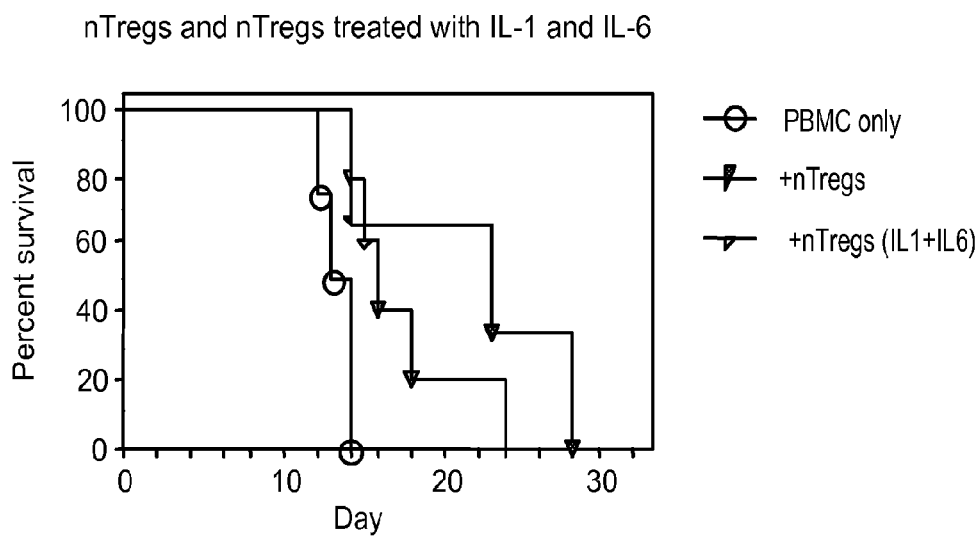
Figure 6G:
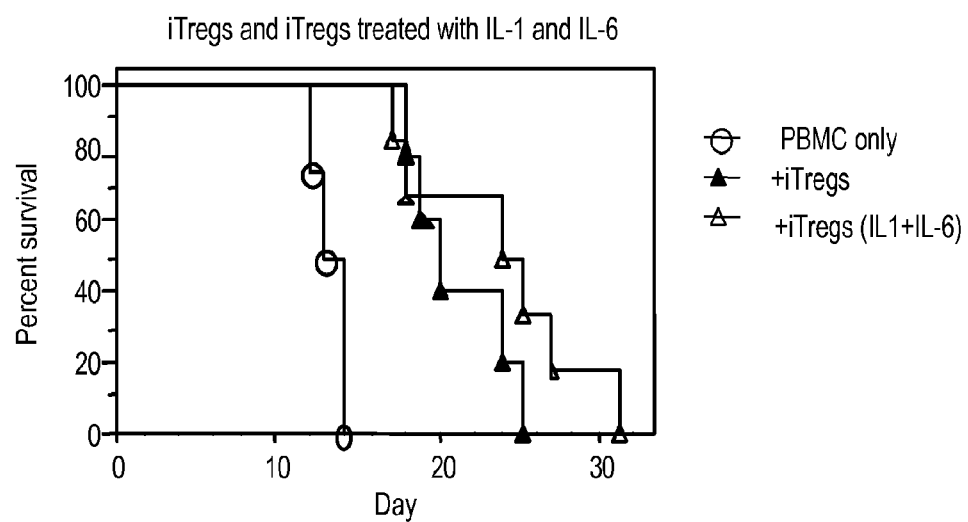

In addition to mouse nTregs, atRA also stabilized FOXP3 expression of human nTregs. nTregs were isolated from human peripheral blood and expanded with anti-CD3/28 coated beads with IL-2 in the presence or absence of atRA. As shown in FIGS. 5A and 5B, some cultures contained IL-1 and/or IL-6. As the nTregs proliferated in culture, the percentage of atRA treated nTregs expressing FOXP3 decreased significantly less than control nTregs, and, correspondingly atRA significantly increased the total number of FOXP3+ cells (p<0.01, *p<0.001). By ten days of culture control FOXP3+ cells increased 5 fold, but atRA treated nTregs increased 20 fold. Thus, treatment of human nTregs with atRA stabilizes FOXP3 and results in a significantly increased yield of expanded suppressor cells.

FIG. 6 shows that the protective activity of human Tregs previously exposed to atRA was significantly greater than control expanded nTregs after these cells were exposed to the cytokines IL-1 and IL-6. These cytokines are generally found in inflammatory exudates and have been shown to decrease the functional properties of nTregs. Immuno-deficient NOD SCID IL-2R gamma chain deficient mice were injected with human blood mononuclear cells. These mice died rapidly from human T cell-induced graft versus host disease (FIG. 6A). These mice also rapidly lost weight (FIG. 6B) and large amounts of human IgG antibody was detected in their serum in one week (FIG. 6C). Both control (untreated) nTregs and induced Tregs treated with atRA prolonged survival, delayed weight loss and prevented IgG antibody production. FIG. 6D-G show the effects of exposing nTregs and Tregs induced with atRA with IL-1 and IL-6. nTregs and Tregs induced with atRA were re-stimulated with anti-CD3/28 beads for three days with these cytokines and then injected into mice. FIGS. 6E-G show that the Tregs induced with atRA were significantly stabilized in comparison to the untreated nTregs (Log Rank Test). These results suggest that nTregs treated with atRA will also similarly be expected to show stability over untreated nTregs.

Example 7 nTregs Isolated from Arthritic Mouse Models

Figure 7A:
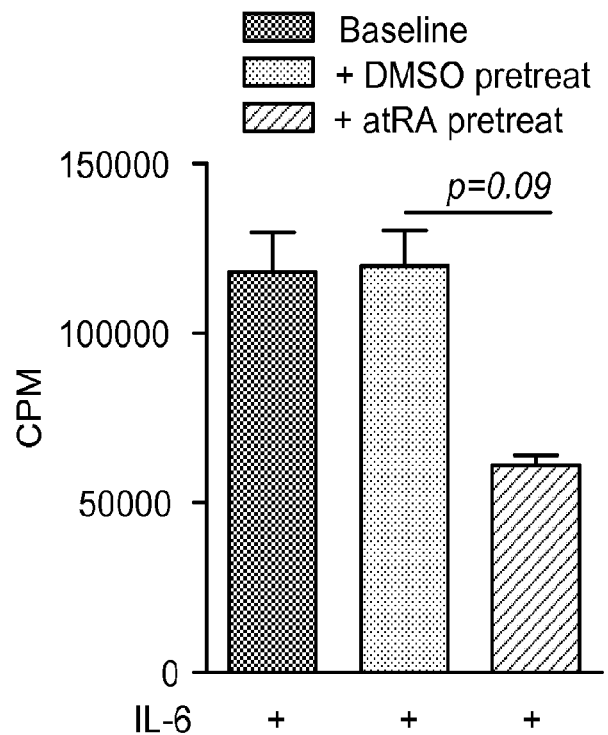
FIG. 7A shows suppressive activity of the treated nTregs as compared to PBS (control) or DMSO treated nTregs.
Figure 7B:
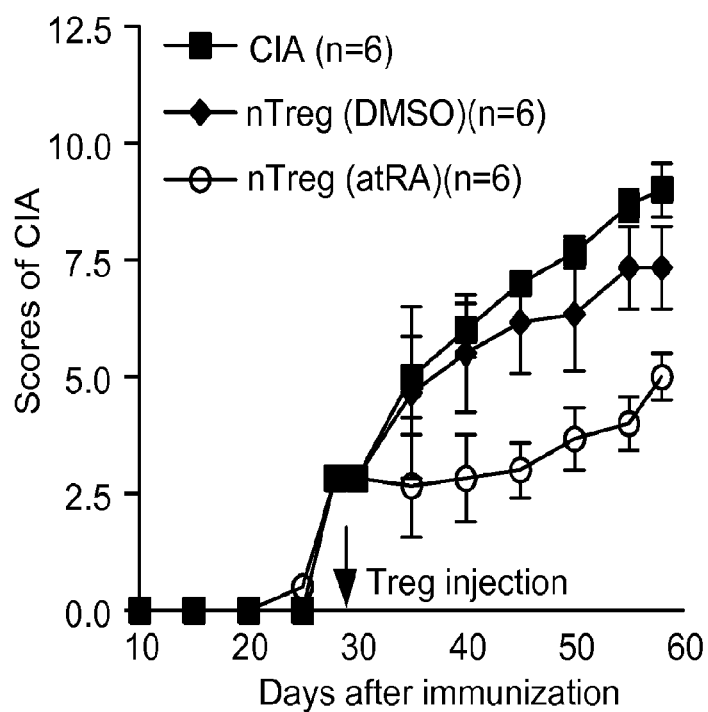
FIG. 7B shows data from mice with established CIA injected with atRA treated nTregs, DMSO treated nTregs, or PBS (control group) treated nTregs.

As shown in FIG. 7, nTregs isolated from mouse models with established autoimmune arthritis (collagen-induced arthritis—"CIA") also show suppressive activity when treated with atRA. For the experiments in FIG. 7A, nTregs isolated from CIA mice were stimulated with immobilized anti-CD3 (1 μg/ml) and IL-6 (10 ng/ml) with and without atRA (0.05 μM) for 7 days. Phenotypic stability was measured by FOXP3 expression and suppressive activity was determined by the proliferation of T responder cells. CMP indicates the value of T responder cells. Values in FIG. 7A indicate the mean±SEM of three independent experiments. In the experiments in FIG. 7B, nTregs from CIA mice were expanded with anti-CD3/CD28 beads (1:5) and IL-2 (100 U/ml)±atRA (0.05 μM) for 4 days. Mice with established CIA were injected intravenously with $1 \times 10^6$ atRA treated nTregs, DMSO treated nTregs or PBS (control group) (n=6/group). The mice were examined every five days after injection and the clinical scores are indicated.

The data in FIGS. 7A and 7B show that nTregs isolated from mice suffering from an immunological disorder can be treated with atRA to develop suppressive activity.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:
1. A method of expanding natural regulatory T cells (nTregs), said method comprising treating a cell culture comprising nTregs with a regulatory composition, wherein said regulatory composition comprises a vitamin A derivative.
2. The method of claim 1, wherein said vitamin A derivative is retinoic acid.

3. The method of claim 2, wherein said retinoic acid is all-trans retinoic acid (atRA).

4. The method of claim 1, wherein said vitamin A derivative is a synthetic retinoid.

5. The method of claim 4, wherein said synthetic retinoid is Am80.

6. The method of claim 1, wherein said regulatory composition further comprises a cytokine.

7. The method of claim 6, wherein said cytokine is TGF-β.

8. The method of claim 1, wherein said regulatory composition further comprises IL-2.

9. The method of claim 1, wherein said regulatory composition further comprises a T cell activator.

10. The method of claim 9, wherein said T cell activator is a member selected from anti-CD3, anti-CD28, or a combination of anti-CD3 and anti-CD28.

11. The method of claim 1, wherein said regulatory composition further comprises an agent that prevents methylation of a gene encoding a transcription factor.

12. The method of claim 11, wherein said agent is a methyltransferase inhibitor.

13. The method of claim 12, wherein said methyltransferase inhibitor is azacytidine.

14. The method of claim 1, wherein said regulatory composition further comprises an agent that is a histone deacetylase inhibitor.

15. The method of claim 14, wherein said histone deacetylase inhibitor is a member selected from trichostatin A, ppAR gamma agonists, and valproic acid.

16. The method of claim 1, wherein said cell culture is submitted to flow cytometry to enrich for FOXP3+ cells prior to and/or subsequent to said treating with said regulatory composition.

17. A method of stabilizing phenotype of nTregs, said method comprising treating said nTregs with a regulatory composition, wherein said regulatory composition comprises atRA.

18. The method of claim 17, wherein said stabilizing comprises rendering said nTregs resistant to Th17 conversion.

19. The method of claim 17, wherein said stabilizing comprises retention of nTreg phenotype in an inflammatory milieu.

20. The method of claim 19, wherein said nTreg phenotype comprises a method selected from expression of FOXP3, suppressive activity, and combinations thereof.

21. A method of decreasing expression of transcription factors associated with inflammatory responses in nTregs, said method comprising treating said nTregs with a regulatory composition comprising atRA.

22. The method of claim 21, wherein said regulatory composition further comprises TGF-β.

23. The method of claim 22, wherein said regulatory composition further comprises IL-2.

24. The method of claim 23, wherein said regulatory composition further comprises a T cell activator.

25. The method of claim 24 wherein said T cell activator is anti-CD3, anti-CD28, or a combination of anti-CD3 and anti-CD28.

26. A method of treating an aberrant immune response or an autoimmune disease in a patient, said method comprising administering treated nTregs to said patient, wherein said treated nTregs are generated by treating a cell culture comprising nTregs with a regulatory composition comprising atRA.

27. The method of claim 26, wherein said regulatory composition further comprises TGF-β.

28. The method of claim 27, wherein said regulatory composition further comprises IL-2.

29. The method of claim 25, wherein said regulatory composition further comprises a T cell activator.

30. The method of claim 29 wherein said T cell activator is anti-CD3, anti-CD28, or a combination of anti-CD3 and anti-CD28.

\* \* \* \* \*